United States Patent [19]

Fujito et al.

[11] 4,282,480
[45] Aug. 4, 1981

[54] APPARATUS FOR HUMIDITY DETECTION

[75] Inventors: Katsuyuki Fujito; Seiro Hasegawa; Takehiko Unoguchi; Atsushi Nishino; Akihiko Yoshida, all of Kadoma, Japan

[73] Assignee: Matsushita Electric Industrial Co., Ltd., Osaka, Japan

[21] Appl. No.: 35,331

[22] Filed: May 1, 1979

[30] Foreign Application Priority Data

May 2, 1978 [JP] Japan .................................. 53-53152
Jul. 17, 1978 [JP] Japan .................................. 53-87443

[51] Int. Cl.$^3$ .......................................... G01R 27/26
[52] U.S. Cl. ............................. 324/61 R; 324/60 CD; 324/61 P
[58] Field of Search ............... 324/61 R, 60 CD, 61 P

[56] References Cited

U.S. PATENT DOCUMENTS 4,065,715  12/1977  Jaffe et al. ....................... 324/60 CD

FOREIGN PATENT DOCUMENTS 2000292  1/1979  United Kingdom ................... 324/61 R

OTHER PUBLICATIONS

Dage, D. H., "Autoranging Digital Capacitance Meter", Popular Electronics, Feb. 1978, pp. 48, 49, 52, 53, 54.

Primary Examiner—Ernest F. Karlsen
Attorney, Agent, or Firm—Lowe, King, Price & Becker

[57] ABSTRACT

Apparatus for humidity detection comprises a humidity sensing element, the electrostatic capacitance of which varies in accordance with the ambient humidity, a fixed capacitor, first and second pulse generating circuits respectively responsive to the sensing element and the capacitor, and a computing circuit responsive to pulses from the first and second pulse generating circuit. The sensing element and the fixed capacitor are respectively charged via resistors to produce first and second pulses in accordance with voltage across the sensing element and the capacitor. The difference between the widths of the first and second pulses is detected in the computing circuit to produce an output pulse indicative of the relative humidity, thereby compensating for undesirable influence due to dielectric loss in the sensing element so as to accurately measure humidity irrespectively of the ambient temperature.

27 Claims, 10 Drawing Figures ained 4,282,480

APPARATUS FOR HUMIDITY DETECTION

FIELD OF THE INVENTION

This invention generally relates to apparatus for humidity detection. More particularly, the present invention relates to such apparatus which employs a humidity sensing element the electrostatic capacitance of which varies in accordance with the ambient humidity.

BACKGROUND OF THE INVENTION

Recently, a humidity sensing element the electrostatic capacitance of which varies in accordance with the ambient humidity is developed. When such a sensing element is utilized as a transducer, an electrical circuit which measures the capacitance of the sensing element is required to produce an electrical signal indicative of the capacitance and therefore the humidity. There are several possibilities for such an electrical circuit. For instance, an A.C. bridge or a resonant circuit may be used to measure the capacitance of the sensing element. However, when employing the above mentioned techniques, troublesome steps are required and furthermore, the electrical circuits for achieving the above mentioned techniques are too complex in construction.

Some inventors of the present invention had already proposed in a published British patent specification (Ser. No.: 2,000,292) a new humidity sensing element the electrostatic capacitance of which indicates the ambient humidity and an electrical circuit for displaying the humidity detected by the sensing element by measuring the capacitance of the sensing element.

According to an electrical circuit which measures the capacitance of the sensing element disclosed in the above mentioned British patent application, the sensing element which is substantially functions as a capacitance, is charged by a suitable charging circuit. The voltage across the capacitance, i.e. the sensing element, is detected to measure a period of time required for the voltage to reach a predetermined value. This method is advantageous compared with the above mentioned methods or techniques since the construction of the electrical circuit is simple. However, this electrical circuit also suffers from a drawback that the measured value is apt to include errors due to dielectric loss in the capacitive element. The dielectric loss of the sensing element varies in accordance with ambient temperature, and therefore, accurate measurement of the humidity is not achieved unless the errors due to the dielectric loss is compensated for.

SUMMARY OF THE INVENTION

The present invention has been developed in order to remove the above mentioned disadvantages and drawbacks inherent to known apparatus for humidity detection, which will be referred to as a humidity sensor hereinafter.

It is, therefore, an object of the present invention to provide a humidity sensor which measures humidity accurately.

Another object of the present invention is to provide a humidity sensor the construction of which is simple.

A further object of the present invention is to provide a humidity sensor which measures humidity quickly.

A still further object of the present invention is to provide a humidity sensor which includes a humidity sensing element the electrostatic capacitance of which varies in accordance with the ambient humidity, while errors due to dielectric loss is compensated for.

A still further object of the present invention is to provide a humidity sensor which comprises a display circuit to visually display the measured humidity.

A yet further object of the present invention is to provide a humidity sensor which comprises a control circuit by which a humidifier and/or a dehumidifier is controlled in order to optimally control the ambient humidity.

A further object of the present invention is to provide a humidity sensor the operation of which is stable and reliable.

According to the present invention, a temperature compensation circuit is employed in order to compensate for the errors due to the dielectric loss inherent to the sensing element. The temperature compensation circuit also functions as an offset circuit which offsets the capacitance of the humidity sensing element, which corresponds to a humidity of zero percent. When it is intended to control the ambient humidity, a reference pulse generating circuit which includes a hysterissis circuit is used in combination with the humidity sensor according to the present invention so as to control the ambient humidity optimally.

BRIEF DESCRIPTION OF THE DRAWINGS

These and other objects and features of the present invention will become more readily apparent from the following detailed description of the preferred embodiments taken in conjunction with the accompanying drawings in which.

DETAILED DESCRIPTION OF THE PREFERRED EMBODIMENTS

Figure 1:
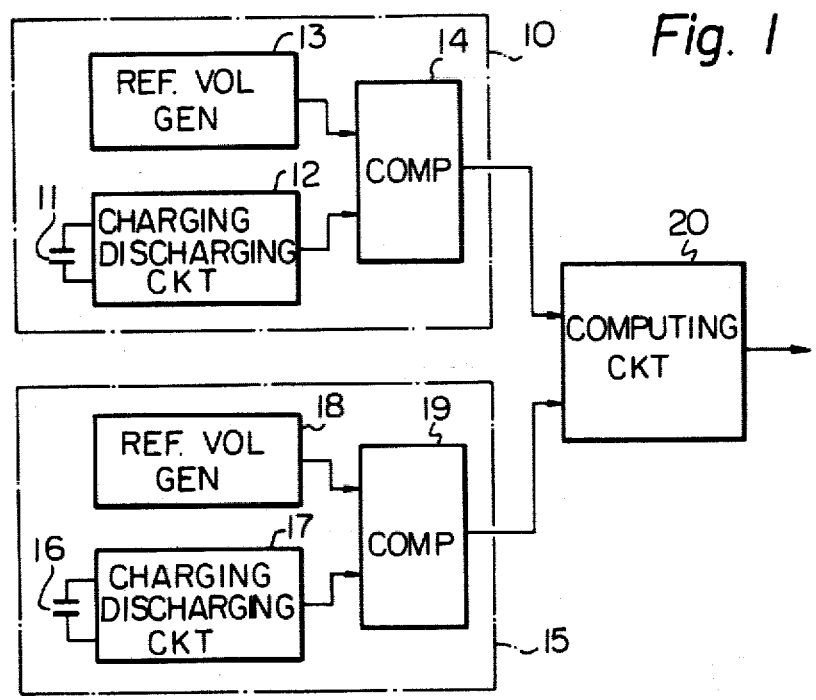
FIG. 1 shows a schematic block diagram of a first embodiment of the humidity sensor according to the present invention.

Referring now to FIG. 1, a schematic block diagram of a first preferred embodiment of the humidity sensor according to the present invention is shown. The humidity sensor comprises a first pulse generator 10, a second pulse generator 15, and a computing circuit 20 which is responsive to the output signals of the first and second pulse generators 10 and 15. The first pulse generator 10 includes a humidity sensing element 11 the electrostatic capacitance of which is variable in accordance with the ambient humidity, a reference voltage generator 13, a charging-discharging circuit 12 and a comparator 14; while the second pulse generator 15 includes a fixed capacitor 16, a second charging-discharging circuit 17, a second reference voltage generator 18, and a second comparator 19. It is to be noted that although the sensing element 11 is illustrated by a symbol of a normal capacitor in the same manner as the capacitor 16 for a simple illustration purpose, the actual equivalent circuit of the sensor element 11 includes at least one capacitor and a plurality of resistors which are connected to the capacitor in parallel and in series. Although the word "humidity" actually means relative humidity, "humidity" is used throughout the specification for convenience.

The sensing element 11 has first and second terminals connected to first and second inputs of the charging-discharging circuit 12 the output of which is connected to a second input of the first comparator 14. The first reference voltage generator 13 has an output connected to a first input of the comparator 14 the output of which is connected to a first input of the computing circuit 20. The capacitor 16, the second charging-discharging circuit 17, the second reference voltage generator 18 and the second comparator 19 are connected in the same manner as in the first pulse generator 10, and therefore the detailed description of the connection of these circuits is omitted. The output of the second comparator 19 is connected to a second input of the computing circuit 20 so that the computing circuit 20 is responsive to the output signals of the first and second pulse generators 10 and 15 to produce an output signal indicative of the ambient humidity.

The circuit shown in FIG. 1 operates as follows. When it is intended to measure the humidity of the ambient air, the first charging-discharging circuit 12 is made operative to charge the sensing element 11. The voltage across the sensing element 11 is detected and is applied to the second input of the first comparator 14, which is responsive to a reference voltage applied to the first input thereof. The voltage across the sensing element 11 increases as time goes and reaches the level of the reference voltage which will be referred to as a threshold hereinafter. The first comparator 14, therefore, generates a pulse signal the leading edge and the trailing edge of which respectively correspond to the time at which the charging operation is started and the time at which the voltage across the sensing element 11 reaches the threshold. In other words, the width of the pulse signal produced by the first comparator 14 indicates an interval for charging the sensing element 11 until the voltage thereof reaches a predetermined value.

The capacitor 16 is charged in the same manner by means of the second charging-discharging circuit 17. However, it is to be noted that the capacitance of the capacitor 16 is fixed and thus does not change in accordance with the humidity. The voltage across the capacitor 16 is detected and is applied to the second input of the second comparator 19, while a variable reference voltage is applied from the second reference voltage generator 18 to the first input of the second comparator 19. The reference voltage applied from the second reference voltage generator 18 is made temperature dependent, and accordingly, the pulse width of the pulse signal produced by the second comparator 19 varies in accordance with the ambient temperature. The second reference voltage will be referred to as a second threshold.

The computing circuit 20 is, therefore, responsive to two pulses, which will be referred to as first and second pulses, respectively applied from the first and second pulse generating circuits 10 and 15. The computing circuit 20 produces a pulse signal by adding or subtracting the pulse widths of the first and second pulses with respect to time.

Figure 2:
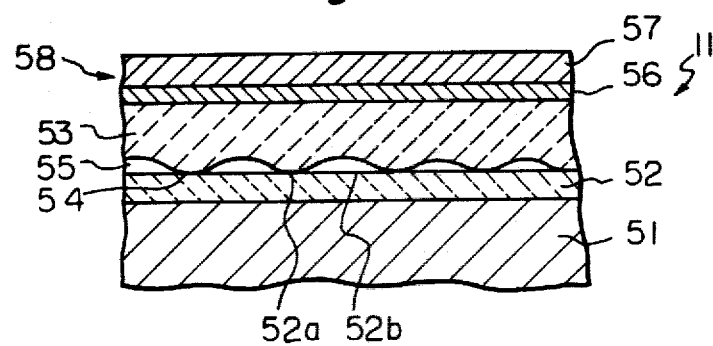
FIG. 2 shows a cross-sectional view of the humidity sensing element shown in FIG. 1.

Reference is now made to FIG. 2 which shows a schematic construction of the humidity sensing element 11 shown in FIG. 1. A reference numeral 51 indicates a substrate, which surves also as a first electrode of this sensing element 11. The substrate 51 is made of a valve metal such as tantalum, alminum, titanium, niobium or hafnium. A surface region of the substrate 51 is oxidized by a known anodization process to give a thin layer or film 52 of a dielectric oxide, e.g. tantalm oxide. A semiconductive metal oxide 53, e.g. manganess dioxide, is provided on the other surface of the thin layer 52. A second electrode 58 of this sensing element 11 has a double layer structure and comprises an inner layer 56 of a first conductive material, such as carbon covering the outside of the semiconductive metal oxide layer 53 either entirely or partly and an outer layer 57 of a second conductive material, such as a metal, overlayed onto the other surface of the inner layer 56 to serve as a counter-electrode to the first electrode 51.

Seemingly, the semiconducting metal oxide layer 53 is in direct contact with the dielectric oxide layer 52 in the entire area of the semiconducting layer 53. However, a real contact between the dielectric oxide film 52 and the semiconducting oxide layer 53 is established only in regions 52a which are distributed throughout the apparent interface between these two layers 52 and 53, so that the outer surface of the dielectric oxide film 52 is left uncoated in regions 52b which also are distributed throughout the aforementioned interface. As a consequence, numerous and microscopically small spaces 55 are defined between the outer surface of the dielectric oxide film 52 and the inner surface of the semiconducting oxide layer 53. Both the semiconducting layer 53 and the conducting layer 58 are made microscopically porous or gas permeable in order to allow moisture to pass through these layers 53 and 58.

The device of FIG. 2 functions as a humidity sensing element on the following principle.

When this device is disposed in an atmosphere containing no moisture, the device has a constant electrostatic capacitance determined by the kind and geometry of the dielectric oxide film 52 and the total area of the coated regions 52a since there occurs no adsorption of moisture through the semiconducting oxide layer 53. Under this condition, the semiconducting layer 53 simply serves as an intermediate electrode layer to take out the capacitance.

When the same device is disposed in a moist atmosphere, the moisture is adsorbed in the semiconducting metal oxide layer 53, which is porous and hence is hygroscopic, and reaches the coated regions 52a of the surface of the dielectric oxide layer 52. Thereafter the adsorbed mosiure intrudes into the spaces 55 and spreads over the uncoated regions 52b. Since the quantity of the adsorbed moisture is proportional to the relative humidity in the atmosphere, the degree of moisture covering on the surface of the dielectric oxide film 52 is proportional to the relative humidity. The adsorbed moisture is not pure water but contains various ions originated from the components of the atmosphere and, in addition, a metal ion such as manganese ion provided by the semiconducting metal oxide layer 53, so that the adsorbed moisture is a sort of electrolyte. Under this condition, a moistened portion of the uncoated regions 52b of the surface of the dielectric oxide film 12 also participates in the takeout of electrostatic capacitance from the dielectric oxide film 52. This means that a change in relative humidity in the atmosphere can be converted into a change in the electrostatic capacitance of the device of FIG. 2.

Figure 3:
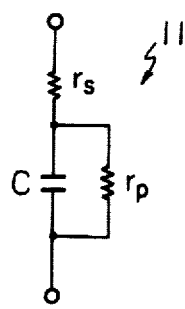
FIG. 3 is a simplified equivalent circuit of the humidity sensing element shown in FIG. 1.

FIG. 3 illustrates a simplified equivalent circuit of the humidity sensing element 11 shown in FIG. 1 and FIG. 2. The simplified equivalent circuit comprises a series circuit of a resistance $r_s$ and a capacitance C, and a resistance $r_p$ connected in parallel with the capacitance C in the same manner as a normal capacitor. These resistances $r_s$ and $r_p$ and capacitance C vary together in accordance with the variation of the ambient temperature and humidity. The value of the series resistance $r_s$ is relatively large compared with a normal capacitor due to the construction of the humidity sensing element 11, while the dielectric loss expressed in terms of tan δ is larger than that of a normal capacitor where most of the dielectric loss is caused by the series resistance $r_s$.

Figure 4:
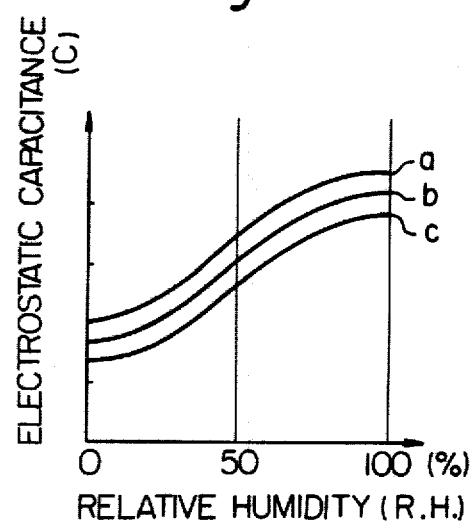
FIG. 4 is a graph showing the electrical characteristics of the humidity sensing element shown in FIG. 1.

FIG. 4 illustrates the electrostatic capacitance variation characteristics with respect to the relative humidity. The horizontal axis of the graph indicates the relative humidity (R.H.), while the vertical axis of the graph indicates the electrostatic capacitance (C) of the humidity sensing element 11. Three characteristic curves "a", "b" and "c" are shown where the curves are made under three different temperatures which are arranged in such a direction that the temperature of the curve "a" is higher than that of the curve "c".

Although the curves shown in FIG. 4 are not of linears, when an approximation by a linear characteristic curve is made, the value of the electrostatic capacitance C of the humidity sensing element 11 will be expressed in terms of the relative humidity X (percent) and the temperature T, as follows:

$$C = \Delta C \cdot X + Co(T) \tag{1}$$

wherein ΔC is the variation in the capacitance per humidity of 1 percent; and

Co(t) is the capacitance which corresponds to a humidity of zero percent at a given temperature T. In the above equation (1), the value of the Co(T) varies as a function of the temperature T, and increases as the temperature T rises.

Let us remember that the width of the pulse signal derived from the first pulse generator 10 of the sensor shown in FIG. 1, is in proportion to the electrostatic capacitance C of the humidity sensing element 11. It will be understood, therefore, that subtracting a period of time corresponding to Co(T) in the above equation (1) from the width of the pulse derived from the first pulse generator 10 results in an accurate proportional relationship between the relative humidity (R.H.) and the pulse width. In the above, it is assumed that Co(T) assumes a positive value. However, Co(T) has a possibility of assuming a negative value since Co(T) is temperature dependent and furthermore, Co(T) is a value on an approximative straight line. In this case, i.e. when the Co(T) is of a negative value, a period of time corresponding to Co(T) may be added to the width of the pulse.

In the above, the basic idea of modification or compensation of the pulse width is described and this technique of modification of the pulse width will be further discussed in detail hereinbelow.

Turning back to FIG. 1, as the first and second charging-discharging circuits 12 and 17, it is possible to use a constant-current circuit or a normal CR charging-discharging circuit in which a resistor is connected in series with a capacitor, i.e. the sensing element 11 or the capacitor 16, so that a constant-voltage is applied to the series circuit.

When utilizing the constant-current charging-discharging technique, a capacitor is charged by a current supplied from a constant-current source, or a capacitor is interposed in the feedback circuit of an operational amplifier to constitute an integrator, and according to this constant-current technique the pulse width will be expressed by:

$$Pw = C \cdot i \cdot Vs \tag{2}$$

wherein

Pw is the pulse width;

i is the constant current; and

Vs is the threshold voltage, such as the voltage of the reference voltage from the first reference voltage generator 13 in FIG. 1.

From the above equation (2) it will be recognized that the pulse width Pw is in proportion to the capacitance C, the current i and the threshold voltage Vs.

On the other hand, according to the above mentioned constant-voltage charging-discharging technique, in which a resistor is connected to a capacitor in series, the pulse width will be expressed by:

$$Pw = -C \cdot R \cdot \ln(1-a) \tag{3}$$

wherein R is the resistance of the resistor connected in series with the capacitor; and $a = Vs/Vcc$ (Vs is the threshold; Vcc is the voltage applied to the series circuit).

From the above equation (3) it will be recognized that the pulse width Pw is in direct proportion to the capacitance C and the resistance R but is not in proportion to the threshold voltage Vs.

Let us remember the electric characteristic of the humidity sensing element 11. The value of the dielectric loss tan δ is relatively large as a capacitive element, where analyzing the electric characteristic by means of an equivalent circuit, most portion of the dielectric loss is due to the series resistance $r_s$ shown in FIG. 3. Therefore, in the constant-current charging technique, a time component corresponding to a value expressed in terms of i × $r_s$ will be included in the pulse width as an error factor.

On the other hand, the pulse width obtained by the constant-voltage charging technique will be expressed by the following equation:

$$Pw = -C \cdot R \cdot \left(1 + \frac{r_s}{R}\right) \cdot \ln\left(\left(1 + \frac{r_s}{R}\right)(1-a)\right) \tag{4}$$

Figure 5:
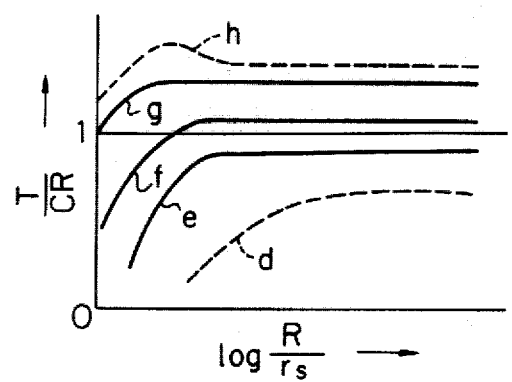
FIG. 5 is a graph showing characteristics of pulses produced in the pulse generating circuit included in the humidity sensor shown in FIG. 1.

FIG. 5 is a graph showing pulse characteristics in terms of log R/$r_s$ plotted along the horizontal axis and Pw/C·R plotted along the vertical axis. The parameter of the graph is α=Vs/Vcc and thus several curves are illustrated in accordance with the parameters α. The variation of the parameters α is as follows:

A curve "d" is obtained when α<0.6; a curve "e" is obtained when α=0.6; a curve "f" is obtained when α=(1−1/e)=0.6321; a curve "g" is obtained when α=0.7; and a curve "h" is obtained when α>0.7;

From this graph of FIG. 5, it will be seen that in the area expressed by 0.6≦α≦0.7 the errors i.e. the deviation from 1, included in the value of T/C·R is so small that the error is negligible throughout a wide range of the values of log(R/r$_s$).

From the foregoing, it will be understood that it is necessary, in order to diminish errors, to use the CR charging-discharging technique and to set the threshold at a value between 0.6 to 0.7 times the voltage of the power supply which supplies the charging current. However, if it is desired to measure a period of time required for a capacitor to be discharged to an extent that the voltage across the capacitor falls below a threshold from the voltage of the power supply, the threshold may be set at a value between 0.3 to 0.4 times the voltage of the power supply, since the voltage curve upon discharging is the same as that upon charging.

Figure 6:
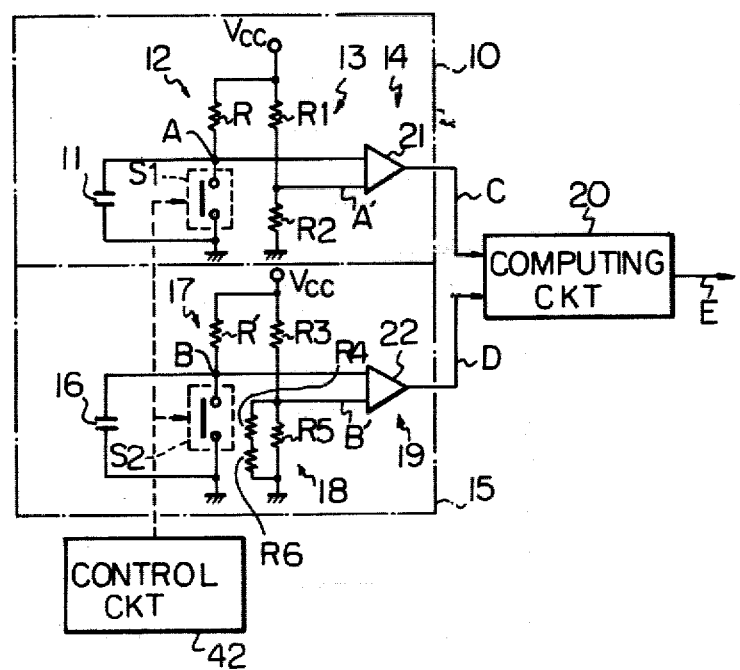
FIG. 6 shows a detailed circuit diagram of the humidity sensor shown in FIG. 1.

Reference is now made to FIG. 6 which shows a detailed circuit diagram of the humidity sensor the block diagram of which is shown in FIG. 1. The same elements and circuits shown in FIG. 1 are designated by the same reference numerals.

The first pulse generating circuit 10 comprises a humidity sensing element 11, a switch S1, three resistors R, R1 and R2 and an operational amplifier 21, while the second pulse generating circuit 15 comprises a fixed capacitor 16, a second switch S2, resistors R', R3, R4, R5 and R6, and a second operational amplifier 22. The humidity sensing element 11, which is shown by a symbol of a normal capacitor, is interposed between a first input of the first operational amplifier 21 and ground, while the first switch S1 is connected in parallel with the humidity sensing element 11. The first input of the first operational amplifier 21 is connected via the resistor R to a positive power supply Vcc, while the second input of the same operational amplifier 21 is connected to a junction between the resistor R1 and R2 which are connected in series between the power supply Vcc and ground. It will be understood that the resistor R and the humidity sensing element 11 constitute an RC series circuit when the first switch S1 is open. In other words, the resistor R and the first switch S1 function as the first charging-discharging circuit 12 shown in FIG. 1. The resistors R1 and R2 constitute a voltage divider and thus functions as the first reference voltage generator 13 to produce a fixed reference voltage. The first operational amplifier 21 functions as the first comparator 14.

The fixed capacitor 16 is interposed between a first input of the second operational amplifier 22 and ground, while the second switch S2 is connected in parallel with the capacitor 16. The first input of the second operational amplifier 22 is connected via the resistor R' to the power supply Vcc, while the second input of the same operational amplifier 22 is connected to a junction between the resistors R3 and R5 which are connected in series between the power supply Vcc and ground. The resistors R4 and R6 are connected in series and this series circuit is connected in parallel with the resistor R5. The resistor R' and the capacitor 16 also constitute an RC series circuit when the second switch S2 is open. The resistor R' and the second switching circuit S2 function as the second charging-discharging circuit 17 shown in FIG. 1. The resistors R3 to R6 constitute a voltage divider so as to function as the second reference voltage generator 18. The resistor R6 is of a temperature dependent type and thus the resistance of the same varies as a function of the ambient temperature. In this embodiment a ceramic resistor (a sort of thermistor), which has a positive temperature coefficient, is used as the resistor R6 so that the voltage at the junction between the resistors R3 and R5 increases as the ambient temperature rises. This means the reference voltage (the second threshold) applied to the second operational amplifier, i.e. the second comparator 14, is made temperature dependent.

The first and second switches S1 and S2 are respectively controlled by a control signal produced by a control circuit 42 to periodically charge and discharge the sensing element 11 and the capacitor 16. The computing circuit 20, for instance, comprises gate circuits, to produce a pulse signal the width of which is determined by the difference between or the sum of the pulse widths of the first and second pulses applied from the first and second pulse generating circuits 10 and 15.

Figure 7:
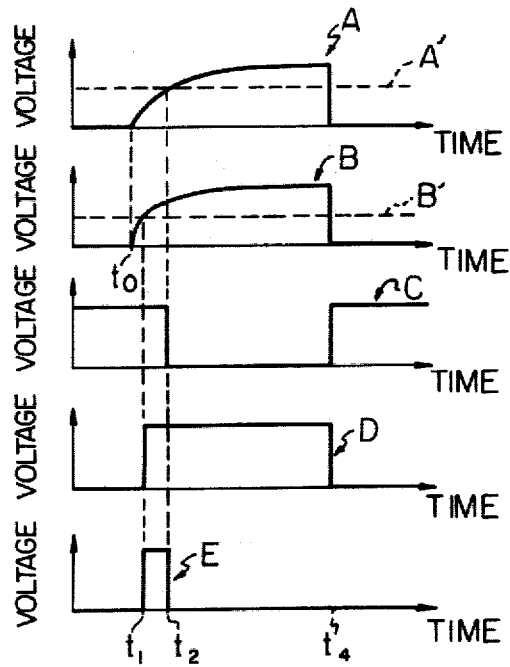
FIG. 7 is a time chart showing various waveforms of signals appearing in the circuit shown in FIG. 6.

FIG. 7 is a time chart showing waveforms of various signals appearing in the sensor circuit shown in FIG. 6. Reference A indicates the waveform of the voltage at one terminal of the humidity sensing element 11, this voltage A is the same as the voltage at the first input of the first operational amplifier 21, while the threshold voltage A' applied from the voltage divider, i.e. the reference voltage generating circuit 13, to the second input of the first operational amplifier 21 is illustrated by a dotted line. Reference B indicates the voltage at one terminal of the capacitor 16, while the other dotted line indicates the threshold voltage B' of the second operational amplifier 22. References C and D respectively indicate the output voltages of the first and second operational amplifiers 21 and 22 which function as first and second comparators 14 and 19. The output pulse of the computing circuit 20 is denoted by a reference E.

As will be understood from the waveforms of the signals, the first comparator 14 produces a high level output signal when the voltage A of the input signal is below the threshold voltage A', and produces a high level output signal when the voltage A equals to or exceeds the first threshold voltage A'. On the other hand, the second comparator 19 produces a low level output signal when the input voltage B is below the second threshold voltage B', and produces a high level output signal when the voltage B equals to or exceeds the second threshold voltage B'.

Assuming that the first and second switches S1 and S2 are made nonconductive at time $t_0$ by the control signal from the control circuit 42, the humidity sensing element 11 and the capacitor 16 start charging. The voltage B of the capacitor 16 reaches the second threshold voltage B' at time $t_1$, and then the voltage of the humidity sensing element 11 reaches the first threshold voltage A' at time $t_2$. The computing circuit 20 produces an output pulse E when the high voltages from the first and second comparators 14 and 19 coincide with each other. Accordingly, the pulse signal E from the computing circuit 20 has leading and trailing edges respectively defined by time $t_1$ and time $t_2$.

The resistor R6 which is included in the second reference voltage generating circuit 18 is a temperature dependent element, such as a thermistor having a positive temperature coefficient. Therefore, the second threshold voltage B' increases as the ambient temperature rises. This means that the time $t_1$ shown in FIG. 7 is variable in accordance with the ambient temperature so that the pulse width of the output signal E varies accordingly although the humidity does not vary. If desired other type thermister which has a negative temperature coefficient may be used, if the construction of the second voltage divider is so changed that the second threshold voltage B' increases as the ambient temperature rises. Since the thermistor R6 is intended to detect the temperature of the humidity sensing element 11, the thermistor R6 is preferably disposed in the vicinity of the humidity sensing element 11.

In each of the first and second pulse generating circuits 10 and 15, inasmuch as the RC-charging and discharging circuit 11, 12 or 16, 17 and the voltage divider 13 or 18 constitute a bridge circuit between the power supply Vcc and ground, the variation in voltage of the power supply Vcc does not influence the widths of the output pulses of the first and second comparators 14 and 19.

It will be understood from the foregoing, that the pulse width of the signal E indicates the relative humidity. The pulse width of the signal E may be measured by counting the number of clock pulses which are regularly spaced, for a period of time defined by the pulse width of the signal E so that the sensed relative humidity may be displayed in digits. Furthermore, the pulse width of the signal E may be converted into a voltage by a suitable integrator so as to control electric devices in accordance with the humidity. These possibilites of the utilization of the sensor according to the present invention will be further described in detail hereinbelow.

Figure 8:
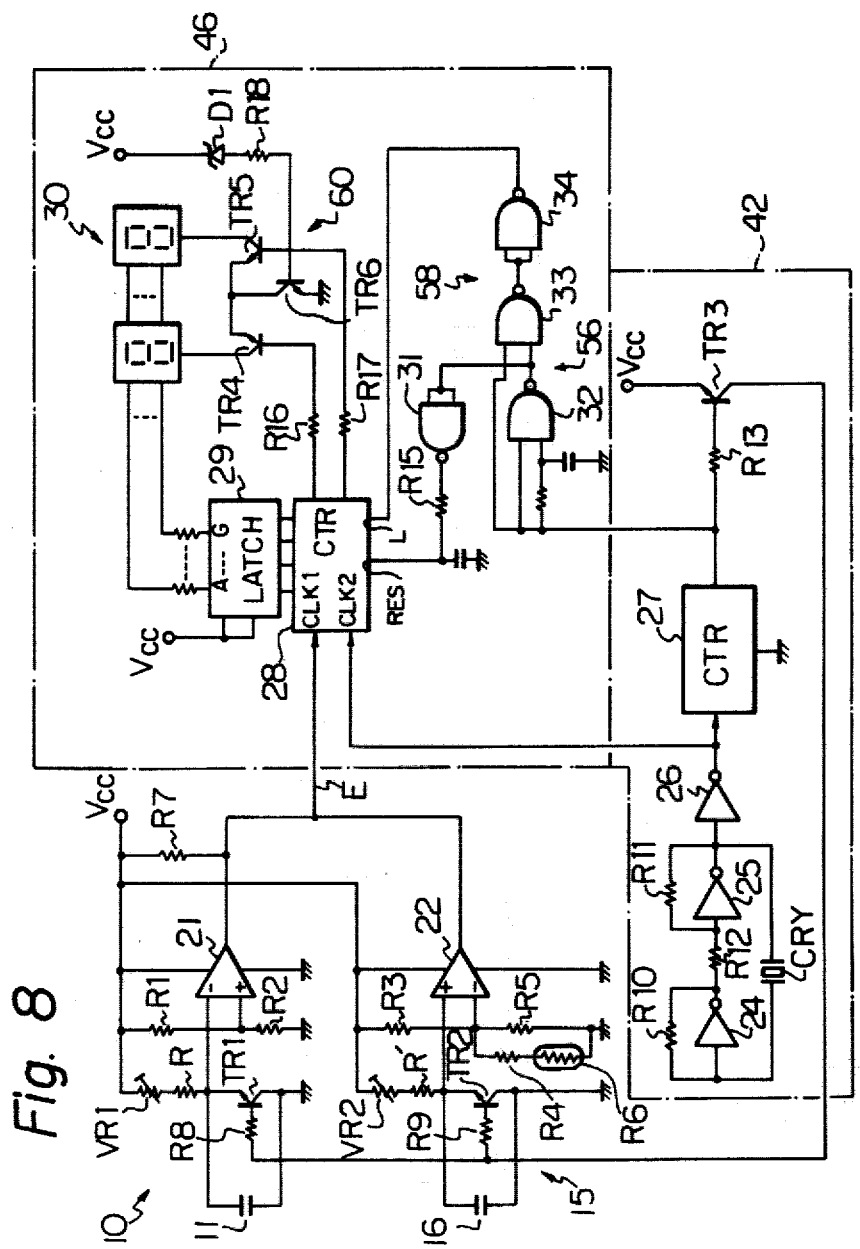
FIG. 8 is a detailed circuit diagram of a humidity display circuit which includes a second embodiment humidity sensor according to the present invention.

Reference is now made to FIG. 8 which shows a detailed circuit diagram of the humidity display circuit including the humidity sensor according to the present invention. The humidity display circuit includes a humidity sensor which is substantially the same as that shown in FIG. 6 and the same reference numerals indicate the same or like elements or circuit. Describing the different points with respect to the construction of the sensor shown in FIG. 6, the first and second swtiches S1 and S2 are replaced by first and second transistors TR1 and TR2, while first and second transistors TR1 and TR2, while first and second variable resistors VR1 and VR2 are additionally provided to be respectively connected in series with the resistors R and R'. Furthermore, the computing circuit 20 is substituted with a wired OR gate circuit, and therefore, each of the operational amplifiers 21 and 22 used as the first and second comparators 14 and 19 has an output stage of an open-collector transistor.

The control circuit 42 comprises four resistors R10 to R13, three NOT gates (inverters) 24 to 26, a crystal CRY, a fourteen stage ripple-carry counter 27, and a transistor TR3. The resistor R10 is connected across the NOT gate 24, while the resistor R11 is connected across the NOT gate 25. The output of the NOT gate 24 is connected to the input of the NOT gate 25, the output of which is connected via the crystal CRY to the input of the NOT gate 24 so that the resistors R10 to R12, the NOT gates 24 and 25, and the crystal CRY constitute a clock pulse generator. The output of the clock pulse generator, i.e. the output of the NOT gate 25 is coupled via the NOT gate 26 to an input of the counter 27, which functions as a frequency divider, so that the frequency of the clock pulses is divided down. The divided signal is applied via the resistor R13 to the base of the transistor TR3 as a bias current.

The emitter of the transistor TR3 (n-p-n type) is connected to the positive power supply Vcc, while the collector of the same is respectively connected via resistors R8 and R9 to the bases of the transistors TR1 and TR2 which function as switching circuits. It is to be noted that these transistors TR1 and TR2 are wired backward with respect to the voltage applied to the collector-emitter paths thereof. The reason for this backward connection of these transistors TR1 and TR2 is that the saturation voltage, i.e. a voltage across the collector-emitter path when conductive, is much smaller than that developed under a normal forward connection. These low saturation voltages are advantageous in order to discharge the sensing element 11 and the capacitor 16 as perfectly as possible, so that both of the sensing element 11 and the capacitor 16 will respectively charge from a level substantially the same as zero level and thus pulse widths are accurately determined.

A reference numeral 46 indicates a display circuit which is responsive to the pulse signal E obtained by the humidity sensor. The display circuit 46 comprises a BCD (binary coded decimal) decade counter 28, a BCD to seven segment decoder/driver (latch) 29, a seven segment display unit 30 and auxiliary circuits. A junction connecting the outputs of the first and second operational amplifiers 21 and 22 is connected to a first clock input CLK1 of the decade counter 28, while the output of the NOT gate 26 is connected to a second clock input CLK2 of the same. The decade counter 29 has four outputs respectively connected to four inputs of the BCD to seven segment decoder/driver 29. The decoder/driver 29 receives electric power from the power supply Vcc to produce a plurality of driving signals at the seven outputs A to G in accordance with the BCD signals from the counter 28. The seven outputs A to G of the decoder/driver 29 are respectively connected to inputs of the seven segment display unit 30 which includes two digit display portions. Two resistors R14 and R15, two capacitors 50 and 52, and four NAND gates 31 to 34 constitute a reset signal generating circuit 56 and a transfer signal generating circuit 58. The reset signal generating circuit 56 is responsive to the output signal of the ripple counter 27 to produce a reset signal which is applied to the reset terminal RES of the decade counter 28. The transfer signal generating circuit 58 is also responsive to the output signal of the ripple counter 27 to produce a transfer signal which will be applied to the load terminal L of the decade counter 28. It will be understood that the information stored in the decade counter 28 is transferred to the decoder/driver 29 in response to the transfer signal, while the stored information is cancelled in response to the reset signal.

Three transistors TR4 to TR6, three resistors R16 to R18 and a diode constitute a time-sharing control circuit 60 which controls the operation of the respective digit display portions of the display unit 30. The time-sharing control circuit 60 is responsive to the clock pulses applied via two auxiliary terminals of the decade counter 28, while the decade counter 28 alternatively transmits two pieces of information (BCD data), each of which is indicative of each digit, by sharing time. In other words, the digit display portions respectively corresponding to the unit digit and the tenth digit are alternatively energized by the transistors TR4 and TR5, while driving signals respectively corresponding to the unit digit and the tenth digit are alternatively supplied to the digit display unit 30 from the decoder/driver 29 at a timing synchronous with the switching operations of the transistors TR4 and TR5. It will be understood that the digit display unit 30 displays the humidity in terms of percent. As the display unit 30 either a LED (light emitting diode) type display unit or a liquid crystal display unit may be used.

The application of the humidity sensor according to the present invention is not limited to the above described humidity display circuit. For instance, the humidity sensor may be used to control the humidity at a desired degree. In order to control the humidity, a humidifier and/or a dehumidifier may be actuated and the ON and OFF operations of the humidifier and/or the dehumidifier is controlled in accordance with the output pulse width of the humidity sensor in view of a preset humidity. A reference pulse is produced in accordance with the preset humidity so that the width of the reference pulse may be compared with the width of the pulse signal indicative of the actual humidity to find the difference therebetween.

Figure 9:
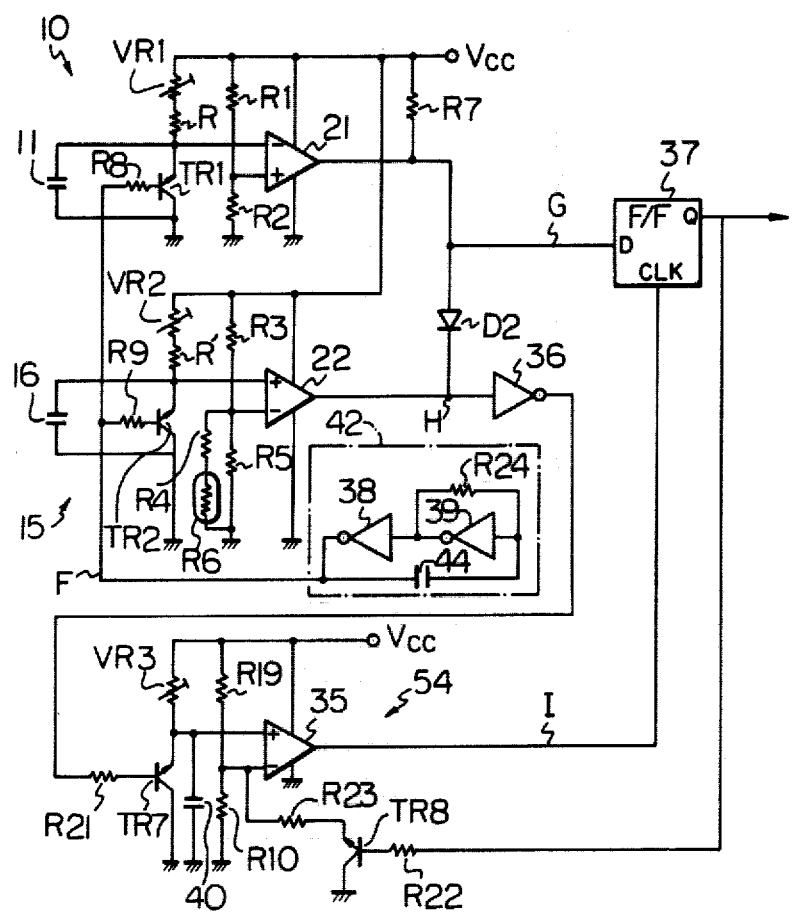
FIG. 9 is a detailed circuit diagram of a humidity control circuit which includes a third embodiment humidity sensor according to the present invention.

Hence, reference is now made to FIG. 9 which shows a humidity control circuit including the humidity sensor according to the present invention. The humidity sensor included in the humidity control circuit is substantially the same in construction as that shown in FIG. 8. The sensing operation is controlled by a control signal produced in the control circuit 42, which includes two NOT gates (inverters) 38 and 39, a resistor R24 and a capacitor 44. The humidity control circuit includes a reference pulse generating circuit which is generally denoted by a reference numeral 54, and a D-type flip-flop 37 in addition to the humidity sensor.

The output of the first operational amplifier 21 is directly connected to the D input of the flip-flop 37, and is further connected to an anode of a diode the cathode of which is connected to the output of the second operational amplifier 22. The output of the second operational amplifier 22 is connected via a series circuit of a NOT gate 36 of TTL-type and a resistor R21 to a base of a transistor TR7 included in the reference pulse generating circuit 54.

The reference pulse generating circuit 54 comprises the transistor TR7, an operational amplifier 35, a variable resistor VR3, a capacitor 40, and a reference voltage generating circuit which includes resistors R10, R19, R22, R23 and a transistor TR8. The variable resistor VR3 is interposed between the power supply Vcc and the emitter of the transistor TR7 the collector of which is grounded. The capacitor 40 is connected in parallel with the emitter-collector path of the transistor TR7 and the emitter of the transistor TR7 is connected to a noninverting input (+) of the third operational amplifier 35. Two resistors R19 and R10 constitute a voltage divider and this voltage divider is interposed between the power supply Vcc and ground, while the junction between the resistors R19 and R10 is connected to an inverting input (−) of the operational amplifier 35. The inverting input (−) is further connected via the resistor R23 to the emitter of the transistor TR8 the collector of which is connected to ground. The base of the transistor TR8 is connected via the resistor R22 to the output Q of the D-type flip-flop 37. The output of the third operational amplifier 35 is connected to the clock input CLK of the D-type flip-flop 37.

Figure 10:
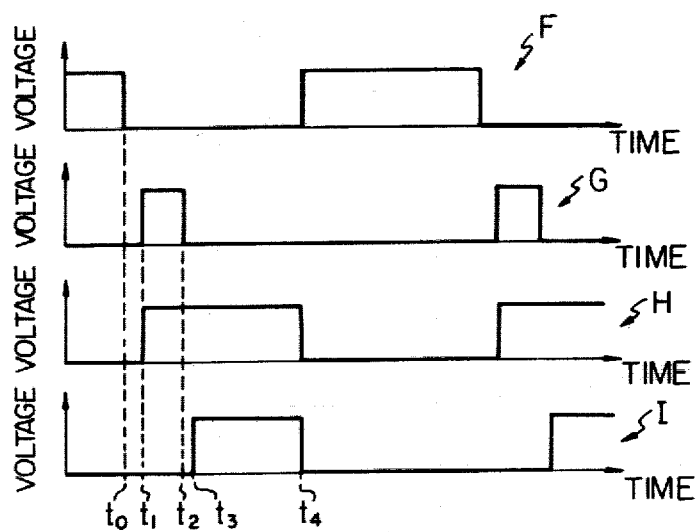
FIG. 10 is a time chart showing various waveforms of signals appearing in the circuit shown in FIG. 9.

The operation of the humidity control circuit shown in FIG. 9 will be described in connection with a time chart shown in FIG. 10. The control signal F generated by the control circuit 42 is applied to the bases of the transistors TR1 and TR2 to control the charging-discharging operation of the first and second pulse generating circuits 10 and 15 in the same manner as in the circuit shown in FIG. 8. The first and second transistors TR1 and TR2 are made nonconductive at time $T_0$ and thus charging operations of the humidity sensing element 11 and the capacitor 16 are respectively initiated at time $t_0$. An output pulse G, which corresponds to the pulse E shown in FIG. 7, is produced at the output of the humidity sensor. The pulse G rises at time $t_1$, and falls at time $t_2$. The voltage of the input signal H of the NOT gate 36 is determined by the output levels of the first and second operational amplifiers 21 and 22 in the following manner.

It is assumed that the output levels of the first and second operational amplifiers 21 and 22 are such that denoted by references C and D in FIG. 7. Here, it is to be noted that each of the operational amplifiers 21 and 22 has an output stage of open-collector transistor so that no voltage comes out from the output of these operational amplifiers 21 and 22 when these operational amplifiers 21 and 22 assume high level. At time before $t_1$ and after $t_4$ only the first operational amplifier 21 assumes high level so that an electric current flows via the resistor R7, which functions as a pull-up resistor, and the diode D2 to the output of the second operational amplifier 22. Therefore, the input level of the NOT gate 36 is low. Between time $t_1$ and $t_2$ both of first and second operational amplifiers 21 and 22 assume high level so that a positive voltage is applied via the resistor R7 and the diode D2 to the input of the NOT gate 36. Between time $t_2$ and $t_4$ no voltage is applied to the input of the NOT gate 36 since the electric current flowing through the resistor R7 directly flows into the output of the first operational amplifier 21. However, the NOT gate 36 functions as if it was receiving a high level input signal since the NOT gate is of TTL type.

The voltage of the input signal H is inverted by the NOT gate 36 and then the inverted signal is applied to the base of the transistor TR7 to control the switching function of the same. Namely, the capacitor 40 is charged from time $t_1$ so that the voltage across the capacitor 40 rises from time $t_1$. It is assumed that the voltage across the capacitor 40 reaches the threshold voltage applied to the inverting input (−) of the operational amplifier 35 at time $t_3$ so that the operational amplifier 35 produces a high level output signal I from time $t_3$. At time $t_4$ the capacitor 40 is discharged and thus the high level output signal I terminates at time $t_4$. The output pulse of the operational amplifier 35 is used in the D-type flip-flop as a clock pulse as will be described hereinafter.

The D-type flip-flop 37 is of an edge-trigger type and thus is arranged to produce a high level output signal at the output Q when the level of the input signal G applied to the input D is high at time $t_3$ at which the clock pulse I rises. In the illustrated example of the time chart of FIG. 10, the level of the input pulse signal G is low at time $t_3$, and therefore, the output of the D-type flip-flop 37 remains at low level. It is assumed that a humidifier (not shown) is actuated in response to the low level output signal of the D-type flip-flop 37. As time goes, the ambient humidity rises and thus the width of the pulse G widens accordingly. This means that the time $t_2$ in FIG. 10 approaches the time $t_3$. When time $t_2$ coincides with time $t_3$, the D-type flip-flop 37 produces a high level output signal by which the humidifier is deenergized. The high level output signal of the D-type flip-flop 37 is maintained until the high level pulse G does not coincide with the leading edge of the clock pulse I upon absence of a clock pulse I.

Assuming that the width of the pulse signal G is so longer than illustrated that a portion of the pulse G coincides with the leading edge of the pulse I and thus the D-type flip-flop 37 produces a high level signal at time $t_3$, the high level output signal is applied via the resistor R22 to the base of the transistor TR8. The transistor TR8 is made conductive so that the resistor R23 forms a parallel circuit with the resistor R10. With this operation the threshold voltage applied to the inverting input (−) of the operational amplifier 35 lowers so that the pulse width of the pulse I widens to an extent in such a manner that $t_3$ is shifted leftward in FIG. 10. Therefore, once the D-type flip-flop 37 is triggered to produce a high level output signal, a portion of the input pulse G coincides with the leading edge of the clock pulse I every time until the width of the pulse G becomes shorter to such an extent that the pulse G does not coincide with the widened width of the pulse I. With this arrangement rapid on/off cycling, which is usually called a hunting phenomenon, of the humidifier is prevented.

While the D-type flip-flop 37 produces a high level output signal, the humidifier is deenergized so that the humidity lowers as time goes. As the humidity drops, the width of the pulse G becomes shorter and shorter and finally, the pulse G does not coincide with the pulse I. At this time the output signal of the D-type flip-flop 37 is inverted to low level to reactivate the humidifier. Upon presence of the low level signal the transistor TR8 is made nonconductive to raise the threshold voltage applied to the operational amplifier 35. Therefore, the operation of the humidifier is prolonged and thus the humidifier will run for a period which is substantially longer than that which would occur should the reference pulse width modification not occur. It will be understood that the on/off operation of the D-type flip-flop and therefore, the operation of the humidifier has a hysterisis characteristic by means of the automatically variable threshold voltage. Therefore, undesirable hunting phenomenon in the operation of the humidifier is prevented.

In the above, it is assumed that the output signal of the D-type flip-flop is used to control the operation of the humidifier. However, a dehumidifier or both of a humidifier and a dehumidifier may be controlled by the output signal of the D-type flip-flop 37 in order to optimally control the humidity.

The variable resistor VR3 is provided to manually set a reference humidity at which it is intended to control the ambient humidity. Since the resistance of the variable resistor VR3 is in accurate proportion to the reference humidity, the dial scale of the variable resistor VR3 has a linear relationship with respect to the reference humidity so that the operation of the humidity control circuit is simple and easy. Furthermore, since the variation in the power supply voltage does not affect on the pulse widths of the pulses produced in first and second pulse generating circuits 10 and 15 and in the reference pulse generating circuit 54 becuase of respective bridge circuit as described hereinabove, the measurement of humidity is performed with high accuracy.

What is claimed is:

1. A humidity sensor comprising:
   (a) a first pulse generating circuit including a humidity sensing element, an electrostatic capacitance of which varies in accordance with the ambient humidity, for producing a first pulse, the width of which indicates the capacitance of said sensing element, said first pulse generating circuit including a first charging-discharging circuit connected to said sensing element for charging said sensing element via a resistor, a reference voltage generating circuit, and a comparator responsive to the voltage across said sensing element and to said reference voltage;
   (b) a second pulse generating circuit including a fixed capacitor for producing a second pulse, the width of which indicates the capacitance of said fixed capacitor, said second pulse generating circuit including a second charging-discharging circuit connected to said fixed capacitor for charging said fixed capacitor, a variable reference voltage generating circuit for producing a reference voltage variable in accordance with the ambient temperature, and a comparator responsive to the voltage across said fixed capacitor and to said variable reference voltage; and
   (c) a computing circuit responsive to said first and second pulses for producing a third pulse by detecting the difference between the widths of said first and second pulses.

2. A humidity sensor comprising:
   (a) a first pulse generating circuit including a humidity sensing element, an electrostatic capacitance of which varies in accordance with the ambient humidity, for producing a first pulse, the width of which indicates the capacitance of said sensing element, said first pulse generating circuit having a first charging-discharging circuit connected to said sensing element for discharging said sensing element via a resistor, a reference voltage generating circuit, and a comparator responsive to the voltage across said sensing element and to said reference voltage;
   (b) a second pulse generating circuit including a fixed capacitor for producing a second pulse, the width of which indicates the capacitance of said fixed capacitor, said second pulse generating circuit having a second charging-discharging circuit connected to said fixed capacitor for discharging said fixed capacitor, a variable reference voltage generating circuit for producing a reference voltage variable in accordance with the ambient temperature, and a comparator responsive to the voltage across said fixed capacitor and to said variable reference voltage; and
   (c) a computing circuit responsive to said first and second pulses for producing a third pulse by detecting the difference between widths of said first and second pulses.

3. A humidity sensor as claimed in claim 1 or 2, wherein said computing circuit comprises an OR gate.

4. A humidity sensor as claimed in claim 1 or 2, wherein said computing circuit comprises a wired OR gate.

5. A humidity sensor as claimed in claim 1, wherein said first charging-discharging circuit comprises a resistor and a first switching circuit connected in series between a power supply and ground, said first switching circuit being connected in parallel with said sensing element.

6. A humidity sensor as claimed in claim 1, wherein said second charging-discharging circuit comprises a resistor and a second switching circuit connected in series between a power supply and ground, said second switching circuit being connected in parallel with said fixed capacitor.

7. A humidity sensor as claimed in claim 1 or claim 2, wherein said reference voltage generating circuit comprises a voltage divider interposed between a power supply and ground.

8. A humidity sensor as claimed in claim 1 or claim 2, wherein said variable reference voltage generating circuit comprises a voltage divider interposed between a power supply and ground, said voltage divider including a plurality of resistors, the resistance of one of said resistors varying in accordance with the ambient temperature.

9. A humidity sensor as claimed in claim 1, wherein said comparator comprises an output stage of an open-collector transistor.

10. A humidity sensor as claimed in claim 1, wherein said comparator comprises an output stage of an open-collector transistor.

11. A humidity sensor as claimed in claim 5, further comprising a control circuit for producing a control signal by which said first switching circuit is controlled.

12. A humidity sensor as claimed in claim 6, further comprising a control circuit for producing a control signal by which said second switching circuit is controlled.

13. A humidity sensor as claimed in claim 1 or claim 2, wherein said control circuit comprises a clock pulse generator.

14. A humidity sensor as claimed in claim 1, wherein said reference voltage is set at a value between 0.6 and 0.7 times the voltage applied to a series circuit of said sensing element and said resistor.

15. A humidity sensor comprising:
(a) a first series circuit of a humidity sensing element the electrostatic capacitance of which varies as a function of the ambient humidity, and a first resistor, said first series circuit being interposed between a power supply and ground;
(b) a first switching circuit connected in parallel with said humidity sensing element;
(c) a first voltage divider interposed between said power supply and ground for producing a fixed reference voltage;
(d) a first comparator responsive to the voltage at a junction between said humidity sensing element and said first resistor, and said fixed reference voltage;
(e) a second series circuit of a fixed capacitor and a second resistor, said second series circuit being interposed between said power supply and ground;
(f) a second switching circuit connected in parallel with said fixed capacitor;
(g) a second voltage divider interposed between said power supply and ground for producing a variable reference voltage, said second voltage divider including a thermister so that said variable reference voltage changes as a function of the ambient temperature;
(h) a second comparator responsive to the voltage at a junction between said fixed capacitor and said second resistor, and said variable reference voltage;
(i) a computing circuit responsive to the output signals of said first and second comparators to produce an output pulse the width of which indicates the relative humidity; and
(j) a control circuit for controlling on/off operations of said first and second switching circuits.

16. A humidity sensor as claimed in claim 15, wherein each of said first and second resistors comprises a variable resistor.

17. A humidity sensor as claimed in claim 15, wherein each of said first and second switching circuits comprises a transistor.

18. A humidity sensor as claimed in claim 17, wherein each of said transistor is wired in such a manner that the collector-emitter path thereof is backward with respect to the voltage applied thereto.

19. A humidity sensor as claimed in claim 1 or 2, in combination therewith of a display circuit, which comprises:
(a) a clock pulse generator for producing a clock pulse train signal;
(b) a counter responsive to said clock pulses and said third pulse for counting the number of said clock pulses for an interval defined by the width of said third pulse;
(c) a decoder/driver responsive to the output data of said counter for producing driving signals; and
(d) a display unit responsive to said driving signals for visually displaying the sensed humidity.

20. A humidity sensor as claimed in claim 19, wherein said display unit comprises two digit displaying portions respectively displaying a unit digit and a tenth digit of the sensed humidity, said two digit displaying portions being controlled to be enabled alternatively by a time-sharing control circuit, said counter transmitting first output data corresponding to said unit digit and second output data corresponding to said tenth digit alternatively in synchronization with the operations of said two digit displaying portions.

21. A humidity sensor as claimed in claim 19, further comprising:
(a) a transfer signal generating circuit for periodically transferring the data stored in said counter to said decoder/driver; and
(b) a reset signal generating circuit for resetting said counter to zero each time the stored data have been transferred to said decoder/driver.

22. A humidity sensor as claimed in claim 15, wherein said control circuit comprises:
(a) a clock pulse generator;
(b) a frequency divider responsive to the clock pulses; and
(c) a switching circuit responsive to the output pulses of said frequency divider to transmit a voltage.

23. A humidity sensor as claimed in claim 22, in combination therewith of a display circuit, which comprises:
(a) a counter responsive to the output pulse of said computing circuit, and to said clock pulses for producing a binary coded decimal output data by counting the number of said clock pulses during an interval defined by the width of said computing circuit output pulse, said counter producing first and second data respectively indicative of the unit digit and the tenth digit of the sensed humidity alternatively;

(b) a decoder/driver responsive to the binary coded decimal output data of said counter for producing driving signals;
(c) a display unit responsive to said driving signals, said display unit including two digit displaying portions of seven-segment type;
(d) a time-sharing control circuit responsive to said clock pulses to alternatively enable said two displaying portions in synchronization with the alternative operation of said counter;
(e) a reset signal generating circuit responsive to the output pulse of said frequency divider to periodically resetting said counter to zero; and
(f) a transfer signal generating circuit for periodically transferring the data stored in said counter to said decoder/driver.

24. A humidity sensor as claimed in claim 1 or 2, in combination therewith of a humidity control circuit, which comprises:
(a) a reference pulse generating circuit for producing a pulse the width of which corresponds to a humidity at which it is intended to control the actual humidity; and
(b) means for comparing the pulse widths of said third pulse and said reference pulse with each other to produce a control signal by which a humidifier and/or a dehumidifier is controlled.

25. A humidity sensor as claimed in claim 24, further comprising a hysteresis circuit responsive to the output signal of said comparing means for changing the width of said reference pulse in accordance with the result of the comparison.

26. A humidity sensor as claimed in claim 24, wherein said comparing means comprises a D-type flip-flop, said D-type flip-flop being of an edge-trigger type and having first and second inputs respectively reponsive to said third pulse and said reference pulse.

27. A humidity sensor as claimed in claim 24, wherein said reference pulse generating circuit comprises:
(a) a series circuit of a resistor and a capacitor, which is arranged to be charged in response to said third pulse;
(b) a comparator responsive to the voltage at a junction between said resistor and said capacitor, and a reference voltage; and
(c) a switching circuit responsive to the output signal of said comparing means for varying said reference voltage.

* * * * *